Figure 1A:
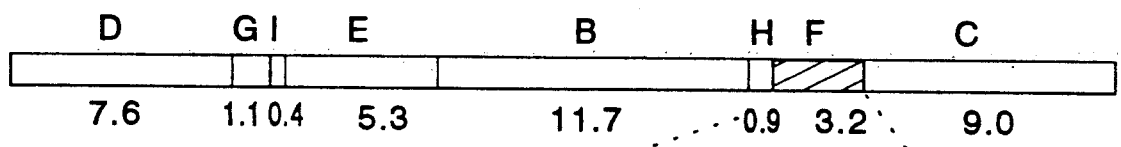

United States Patent [19]

Dhaese

[11] Patent Number: 5,202,237

[45] Date of Patent: Apr. 13, 1993

[54] **METHOD OF REGULATING EXPRESSION IN *BACILLUS SUBTILIS* USING OPERATOR DNA**

[75] Inventor: Patrick Dhaese, Drongen, Belgium

[73] Assignee: Solvay & Cie, Brussels, Belgium

[21] Appl. No.: 670,498

[22] Filed: Mar. 15, 1991

Related U.S. Application Data

[63] Continuation of Ser. No. 175,047, Mar. 30, 1988, abandoned, which is a continuation-in-part of Ser. No. 171,941, Mar. 23, 1988, abandoned.

[30] Foreign Application Priority Data

Mar. 30, 1987 [NL] Netherlands ............ 87.00740

[51] Int. Cl.$^5$ ............... C12N 15/63; C12N 15/75; C12N 15/09
[52] U.S. Cl. .................. 435/69.1; 435/172.3; 435/252.31; 435/320.1; 435/839; 935/40; 935/43
[58] Field of Search ............ 536/27; 435/69.1, 172.3, 435/320.1

[56] References Cited

FOREIGN PATENT DOCUMENTS 0152830  8/1985  European Pat. Off. .

OTHER PUBLICATIONS

Osburne et al., *J. Bact.* 163(3):1101–1108 (1985).
Van Kaer, et al. *J. Mol. Biol.* 197:55–67, (1987).
Dhaese et al., *Nucl. Acid. Res.* 13(15):5441–5455, (1985).

*Primary Examiner*—Richard A. Schwartz
*Assistant Examiner*—Johnny F. Railey, II
*Attorney, Agent, or Firm*—John P. White

[57] ABSTRACT

This invention relates to operator DNA specific for the repressor of φ105 and to the use thereof. The sequence of the operator DNA is 5'-GACGGAAATACAAG-3', 5', GTCGGAAATACAAT-3', 5'-GACGAAATTCAAG-3' or 5'-GTCGTGAATACCAT-3.

3 Claims, 8 Drawing Sheets

Figure 4b

```
           C_φ105
       BclI
5' TGAT CAC CTATCTCCTTTACAACACATAGTGCCTCACTGTGCCACTGTGT CTTGT
        ←                                                  50
          O_R4         P_M→
                       ←
GGCATGACACA ATTATA GTATCCGAAT ATACAA T ACTAAAAAA GACGGAAATACAAG TATTTTTTAGTAATT
 O_R2        "-10"            "-35"    O_R5                         P_R→
                                         +1                         ←
GAATACCA TACAAT T AAAAATGCTTGAATTTCGTCAAATTTCGACTT TTACA AAATGTCGT
         "-10"                                       HindIII
                                                            ORF 3   ATG GGG    7
                                                                    Met  Gly
                                              200
AAG CTT GGG                                                    Lys Lys Leu Gly
                                                               ←
GAATACC ATTAGACATACCTTAACGGGAGGTGATAATC
   O_R3        +1                          ATG CTG GAT GGG AAA ATG GCG AAG GCA 27
                                           Met Leu Asp Gly Lys Lys Leu Gly
                           250

GCT TTA ATT AAG GAC AAA AGA AAA GAA AAG CAC TTG AAA CAG ACA GAA ATG GCG AAG GCA 27
Ala Leu Ile Lys Asp Lys Arg Lys Glu Lys His Leu Lys Gln Thr Glu Met Ala Lys Ala
                              300
CTG GGT ATG TCC AGA ACT TAT CTC TCT GAT ATC GAA AAC GGC AGA TAT CTG CCG AGT ACA 47
Leu Gly Met Ser Arg Thr Tyr Leu Ser Asp Ile Glu Asn Gly Arg Tyr Leu Pro Ser Thr
                                350                                  400
AAA ACA CTT TCC AGA ATA GCG ATT TTA ATA AAT CTG GAT TTA AAT GTG TTA AAA ATG ACG 67
Lys Thr Leu Ser Arg Ile Ala Ile Leu Ile Asn Leu Asp Leu Asn Val Leu Lys Met Thr
  O_R3                                              ▼                   450
GAA ATA CAA GTA GTT GAG GAG GGT GGA TAT GAT AGA GCT GCC GGC ACA TGT AGA AGA CAG 87
Glu Ile Gln Val Val Glu Glu Gly Gly Try Asp Arg Ala Ala Gly Thr Cys Arg Arg Gln
                          500
GCT TTA TGAGATTTTTATGAAACTATCAGTTCCAAGGTTGCTTGAGAAGAAGCCCTGAGAAGGAGAAGCCGAA  600
Ala Leu xxx                       550
                     HaeIII                                      BclI
TGCGGAAAAGAAAAGGGCGGCTTGACCTCGCGGCCTTCTTCGCTGAATTTGAACAAATGATGATCA  3'
                                                              650
```

```
                   Helix 2          wending        Helix 3
         ┌─┐               ┌─┐                ┌──┐ ┌──┐ ┌─────┐
   c     │Q│ V Q L │A│ E K A N L │S R│ S │Y L│ A │D I E│ R
  ø105 20│ │       │ │           │   │   │   │   │     │    39
         └─┘       └─┘           └───┘   └───┘   └─────┘

┌─┐       ┌─┐           ┌───┐   ┌───┐   ┌─────┐
  ORF3   │Q│ T E M │A│ K A L G M │S R│ T │Y L│ S │D I E│ N
       21└─┘       └─┘           └───┘   └───┘   └─────┘    40
```

METHOD OF REGULATING EXPRESSION IN *BACILLUS SUBTILIS* USING OPERATOR DNA

This is a continuation of application Ser. No. 175,047, filed Mar. 30, 1988, now abandoned, which is a continuation-in-part of application Ser. No. 171,441, filed Mar. 23, 1988, now abandoned.

This invention relates to operator DNA as well as recombinant vectors, specifically recombinant plasmids containing this operator DNA, to prokaryotic and eukaryotic cells and organisms transformed using such recombinant vectors, and to the use of the operator DNA, for example for regulating the expression of homologous or heterologous structural genes in prokaryotic and eukaryotic cells and organisms by means of the regulatable presence of the associated repressor.

This invention is in the field of DNA recombinant engineering and is based in part on the identification of DNA sequences operative as an operator in the lysogenic *Bacillus subtilis* phage $\phi$105, that is to say, which render possible a regulation of the expression of genes by interaction with $\phi$105 repressor protein. The operator sequences in question are in the EcoRI-F immunity region (immF) of phage $\phi$105, which region contains two promoters ($P_M$ and $P_R$) in opposite orientations. The presence of repressor protein turns out to stimulate transcription from $P_M$ and to repress $P_R$.

EP-A-0182562 describes a process for inducing gene expression in gram positive bacteria, such as Bacillus, Streptomyces, Corynebacterium, Clostridium and Staphylococcus species by varying the temperature. For this purpose the bacteria in question are transformed so that they contain at least two different types of plasmids, namely, a first type of plasmids containing a heterologous structural gene whose expression can be regulated under the control of a regulation sequence comprising a promoter suitable for the bacterium selected, and a second type of plasmids containing a gene coding for a repressor capable of interaction with the regulation sequence in the first type of plasmids, whereby the expression of the repressor gene can be regulated owing to the presence in the second type of plasmids of a temperature-sensitive replication origin.

More particularly, the cited publication describes transformed *Bacillus subtilis* bacteria containing a pPGV10$\phi$ or pPGV301 plasmid as a representative of the first type of plasmids and a pCGV28 plasmid as a representative of the second type of plasmids. The pPGV10$\phi$ and pPGV301 plasmids contain the chloramphenicol acetyl transferase (cat-86) gene as a model for the heterologous structural gene, which cat-86 gene originates from the pPL603 plasmid. pPGV10$\phi$ and pPGV301 plasmids have been constructed starting from the pPL603 and pUC8 based cointegrate plasmid pPGV2 (7.4 kb) which in addition to $Ap^R$ and $Km^R$ genes contain a multiple cloning site just ahead of the promoterless cat-86 gene. The pPGV10$\phi$ plasmid was obtained by inserting in one of the unique restriction sites of the multiple cloning site, namely, the BamHI site, a Sau3A fragment of 650 bp, originating from 105 DNA, which is located in the EcoRI-F fragment of $\phi$105 DNA. Apparently the pPGV10$\phi$ plasmid consequently contains the cat-86 gene under the control of a regulation sequence comprising a $\phi$105 operator and the $\phi$105 early promoter $P_R$. The pPGV301 plasmid was constructed from a pPGV138$\phi$ plasmid based on pPGV2, which contains the cat-86 gene under the control of the strong $P_{138}$ promoter without the presence of a $\phi$105 operator. By inserting a $\phi$105 operator containing 231-bp RsaI-HaeIII fragment of the SmaI site of pPGV138$\phi$, the pPGV301 plasmid was obtained, which contains the strong $P_{138}$ promoter and a $\phi$105 operator sequence just upstream of the cat-86 gene.

The pCGV28 plasmid is based on the *Bacillus subtilis* replicon pE194, which in addition to an $Em^R$ gene contains a temperature-sensitive origin of replication which at temperatures of 45° C. and higher prevents replication. As pE194 exhibits a low copy number in *B. subtilis* and in addition contains few favourably located unique restriction sites, it was united with pUC4 to form the cointegrate plasmid pCGV4 (6.4 kb), whereafter the pCGV28 plasmid (6.8 kb) was obtained by ligation of the $\phi$105 EcoRI-F fragment with EcoRI-treated pCGV4, which plasmid contains the $\phi$105 repressor gene. Similarly, the pCGV14 plasmid (6.0 kb) was obtained by cloning the $\phi$105 PstI-PstI fragment (2.3 kb) containing the $\phi$105 repressor gene in pE 194 copy-6.

Now, the cited publication does indicate $\phi$105 DNA fragments which, on the ground of the experiments conducted may be assumed to comprise at least one $\phi$105 operator sequence, but there is no evidence of any insight into the structure and exact position of the operator sequence. This lack of insight into the exact nature of the operator bars optimization and a wider use, also in cells and organisms other than just gram positive bacteria, of the process described. The same applies to other applications of the operator-repressor interaction other than just within the framework of a process for regulatable gene expression, for example, in a process for selecting DNA fragments containing the operator from a mixture of DNA fragments, utilizing the linkage of the repressor to the fragments sought.

We have now acquired an insight into the structure of the $\phi$105 operator, and also into the form and locations of its presence in the $\phi$105 DNA, and in subtle structural variations which affect the affinity of the repressor to the operator sequence. This new insight makes it possible to remove the shortcomings of the knowledge disclosed in the cited publication. More particularly, it is now possible to optimize the process of EP-A-O 182 562 by omitting or removing superfluous and/or interfering DNA fragments to enhance the effect of the repressor on the expression of the structural gene by using several copies of the operator in tandem, to adjust the affinity of the repressor to the operator at a desired level by using a suitably selected structural variant of the operator, to use fully synthesized operator fragments instead of being dependent on the availability of $\phi$105 DNA, to apply the process also to cells and organisms other than gram positive bacteria, specifically to eukaryotics, such as yeasts, moulds, plant cells, animal cells and human cells, and to use the operator-repressor interaction for other purposes, such as for detecting and isolating operator-containing DNA fragments from a mixture of DNA fragments.

Figure 4A:
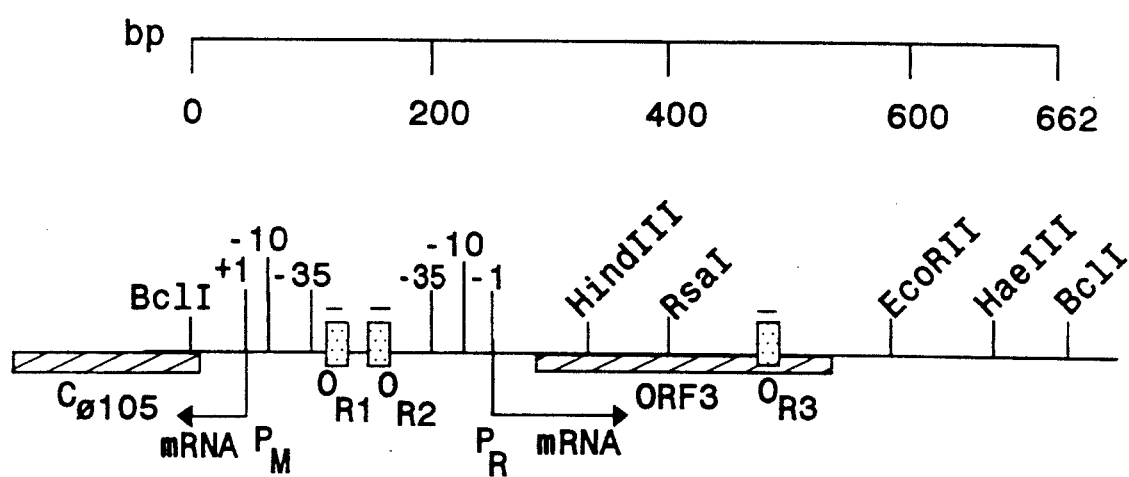

It has been found that the EcoRI-F fragment of $\phi$105 DNA contains the following $\phi$105 repressor specific operator sequences:

(a) the sequence 5'-GACGGAAATACAAG-3', which surprisingly is present thrice in direct repetition, namely, twice in the region between the $P_M$ and $P_R$ promoters and once in the ORF3 gene, approximately 250 bp downstream of $P_R$; these operator sequences will be designated herein as $O_{R1}$, $O_{R2}$ and $O_{R3}$, respectively, are shown in the accompanying FIG. 4.

(b) the sequence 5'-GTCGGAAATACAAT-3', which overlaps the −35 region of the $P_M$ promoter and is designated herein as $O_{R4}$.

(c) the sequence 5'-GACGAAATTCAAG-3', which is located on the non-coding strand between $O_{R2}$ and the $P_R$ promoter and is designated herein as $O_{R5}$.

(d) the sequence 5'-GTCGTGAATACCAT-3', which occurs between the −35 and −10 regions of the $P_R$ promoter and is designated herein as $O_{R6}$.

The structure of these operator sequences is a big surprise by reason of the complete absence of twofold rotational symmetry, which was observed in all operator sequences of gram negative bacteria and phages identified before. In the case of the phage λ operators, for which detailed information about the structure of the repressor protein operator DNA complex is available, the twofold rotational symmetry implies that each site binds a repressor dimer. Such a symmetrical bonding does not appear to occur with phage $\phi 105$, and is has been shown experimentally that, indeed, the effect of repressor binding differs depending on the orientation of the operator relative to the transcription direction. This would explain at least partially why the regulation of the promoters $P_M$ and $P_R$ of phage $\phi 105$ is different: $P_M$, which initiates the transcription of the $\phi 105$ repressor gene, is, as stated before, stimulated by the repressor, while the early promoter $P_R$ is suppressed by the repressor.

It is also surprising that three perfectly identical copies of the operator sequence (a) are present, which may be assumed to possess a very comparable affinity to the repressor. In the Escherichia coli phage λ, on the other hand, subtle structural variations in the individual binding sites of the $O_L$ and $O_R$ regions are present, which form the basis for the differences in affinity relative to the cI and cro products.

Furthermore, it turns out that the $O_{R1}$ and $O_{R2}$ sequences do not overlap with the RNA polymerase recognition sites of $P_M$ and $P_R$. $O_{R1}$ is located at −59 to −46 relative to the $P_M$ starting position, and $O_{R2}$ is more than 50 bp upstream of the "−35" region of $P_R$. What is also surprising is the location of $O_{R3}$, namely, 224 bp downstream of the $P_R$ initiation site in the ORF3 gene. As determined experimentally, this large distance between the operator sequence and the RNA polymerase initiation site is not an impediment for the function of the operator. This data promotes a large freedom of choice with regard to the promoter and, hence, of the host. Partly owing to the possibility of using several copies of the operator sequence in tandem, which makes it possible to attain a strong repression, it is also possible to use very strong promoters, such as the bacteriophage T5 or veg gene signals.

As regards the operator sequence $O_{R4}$, it appears to be plausible that, of the operator sequences identified, this has the weakest affinity to the $\phi 105$ repressor, so that the effect of $P_M$ and, hence, the synthesis of repressor is not blocked until after high concentrations of repressor have been reached. A realistic possibility also appears to be that the operator sequence $O_{R4}$ has a high affinity to the ORF3 product. The ORF3 gene is topologically equivalent to λ cro. When the BclI fragment containing the ORF3 gene is transferred to a multicopy plasmid in B. subtilis, immunity from superinfection with $\phi 105$ is obtained. The ORF3 product is a polypeptide of 89 amino acids long, a portion of 20 amino acids of which conforms to the requirements for an α-helix/-wending/α-helix configuration, which is characteristic for DNA binding proteins. Compared to the analogous region in the $\phi 105$ repressor protein, there is strong homology. This raises the suspicion that the ORF3 product will recognize DNA sequences comparable to the $\phi 105$ repressor protein. It is quite conceivable, therefore, that the ORF3 product has a preference for $O_{R4}$ and, by interaction therewith, prevents the transcription of the repressor gene ($c\phi 105$).

With regard to $O_{R5}$ and $O_{R6}$, it is unknown, for the present, how the affinity between these operator sequences and repressor relates to the affinity between the other operator sequences and repressor.

The above hypotheses, however, are intended by way of illustration only, and must not be construed as limiting the invention here described in any way.

The here described invention is primarily embodied in DNA consisting of at least one sequence of 13–14 basepairs having the following structure: 5'-GN$^1$CGNN$^2$AATN$^3$CN$^4$AN$^5$-3', where N represents a bond or any of the nucleotides G, C, A, T, and N$^1$ - N$^5$ each represent one of the nucleotides G, C, A, T.

Specific preferred embodiments thereof are DNA consisting of the 14 basepairs sequence 5'-GACGGAAATACAAG-3'; DNA consisting of the 14 basepairs sequence 5'-GTCGGAAATACAAT-3'; and DNA consisting of the 13 basepairs sequence 5'-GACGAAATTCAAG-3'; and DNA consisting of the 14 basepairs sequence 5'-GTCGTGAATACCAT-3'.

The DNA according to the invention may have been isolated from $\phi 105$ DNA, but has preferably been obtained by chemical synthesis.

The invention also covers DNA having a length longer than 14 basepairs comprising the sequence specified and obtained at least in part by chemical synthesis. One example is DNA which, in addition to the operator sequence present in one or several copies contains additionally one or several restriction sites (i.e. restriction enzyme recognition sequences) by virtue of which it can be readily manipulated. The DNA may also comprise a suitable promoter and/or a selected structural gene. In addition DNA with a longer length than 13–14 basepairs preferably comprises several supplementary A-T basepairs, so that the surrounding DNA can be designated as A-T rich DNA.

The invention is further embodied in a recombinant vector, specifically recombinant plasmid, comprising vector DNA, a promoter and DNA oriented in the transcription direction of the promoter, as defined hereinbefore. Although the operator sequence according to the invention can, in principle, be located upstream, within, or downstream of, the promoter, it is preferred, by reason of a great flexibility in the choice of the promoter and for constructional engineering reasons, for the operator sequence to be located downstream of the promoter, such as, for example, at a distance in the order of 220 basepairs, counted from the promoter initiation site.

In order that, even in the case of strong promoters, good repression may be possible, it is generally preferred for the recombinant vector to comprise several copies in tandem of the operator sequence. Preferably, at least one copy is located upstream of the promoter.

Downstream of the promoter and operator, the vector will generally contain a, homologous or heterologous, structural gene whose regulatable expression is desired. In the experiments so far conducted, we selected as a model the cat-86 gene, but it will be clear to those skilled in the art that, and how, this gene can be replaced by other structural genes.

The invention is further embodied in cells and organisms transformed using such a recombinant vector according to the invention. The term "transformed" is used herein in the broad meaning of "genetically modified" and accordingly comprises variants in which at least the operator sequence has been incorporated into the genome of the host. There is, however, a particular preference for a transformation which results in the cells or organisms containing one or more recombinant plasmids according to the invention.

As regards the host to be used, there are in principle no limitations: both prokaryotics (such as gram positive and gram negative bacteria) and eukaryotics (such as yeasts, moulds, plants, animals and Man) are suitable as a host, in particular plant cells, animal cell lines and human cell lines cultured in vitro. The interaction between repressor protein and operator DNA is in fact not linked to specific organisms. On the other hand, it will be necessary for the promotor to be attuned to the host contemplated, so that transcription of the structural gene can be realized in the host. Generally, there will also be a correlation between the gene to be expressed and the nature of the host, but in many cases there are no mandatory limitations in this regard.

In a particularly preferred embodiment, the cells and organisms transformed as described above are also provided with the genetic information for the formation of the $\phi 105$ repressor and with a means by which the formation of the $\phi 105$ repressor can be regulated, in particular in the form of one or more recombinant plasmids consisting of a temperature-sensitive replicon and a functional $\phi 105$ repressor gene inserted therein. Although this repressor gene may be under the control of the natural $P_M$ promoter, it is preferred for the repressor gene to be under the control of a different promoter, at least under the control of a regulation sequence which does not contain competitive operator sequences, such as the $O_{R1}$ and $O_{R2}$ sequences of $\phi 105$ DNA.

Finally, the invention also comprises the use of the new operator DNA for regulating, by means of the regulatable presence of the $\phi 105$ repressor, the expression of a, homologous or heterologous, structural gene in prokaryotic and eukaryotic cells and organisms, and the use of the new operator DNA as a label for recombinant DNA for the purpose of detecting the recombinant DNA in, and isolating it from, a DNA mixture containing the recombinant DNA by means of $\phi 105$ repressor.

Figure 1B:
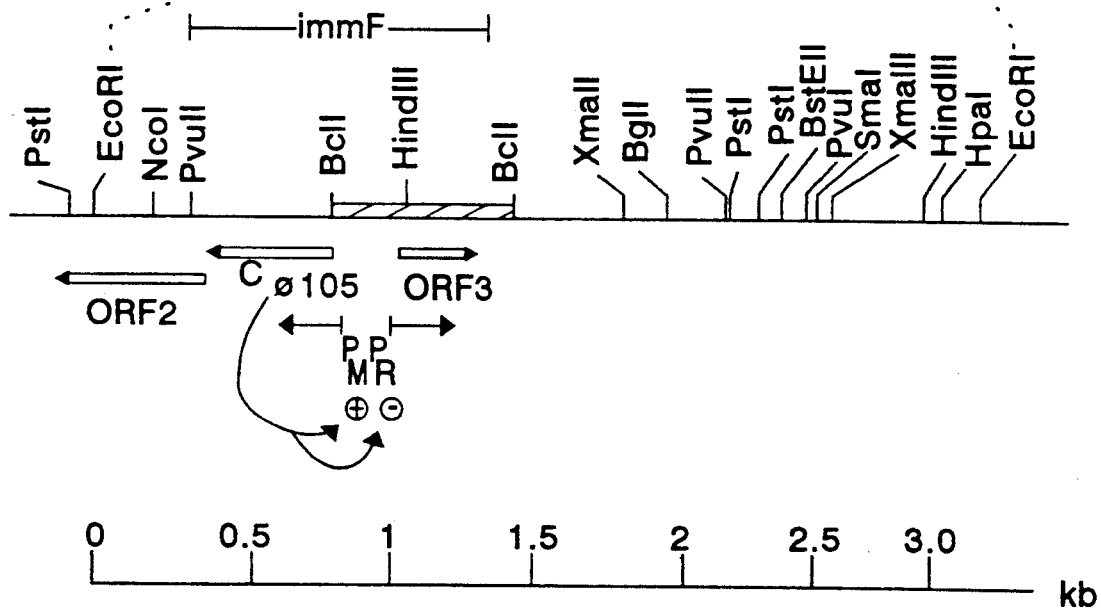
Figure 2:
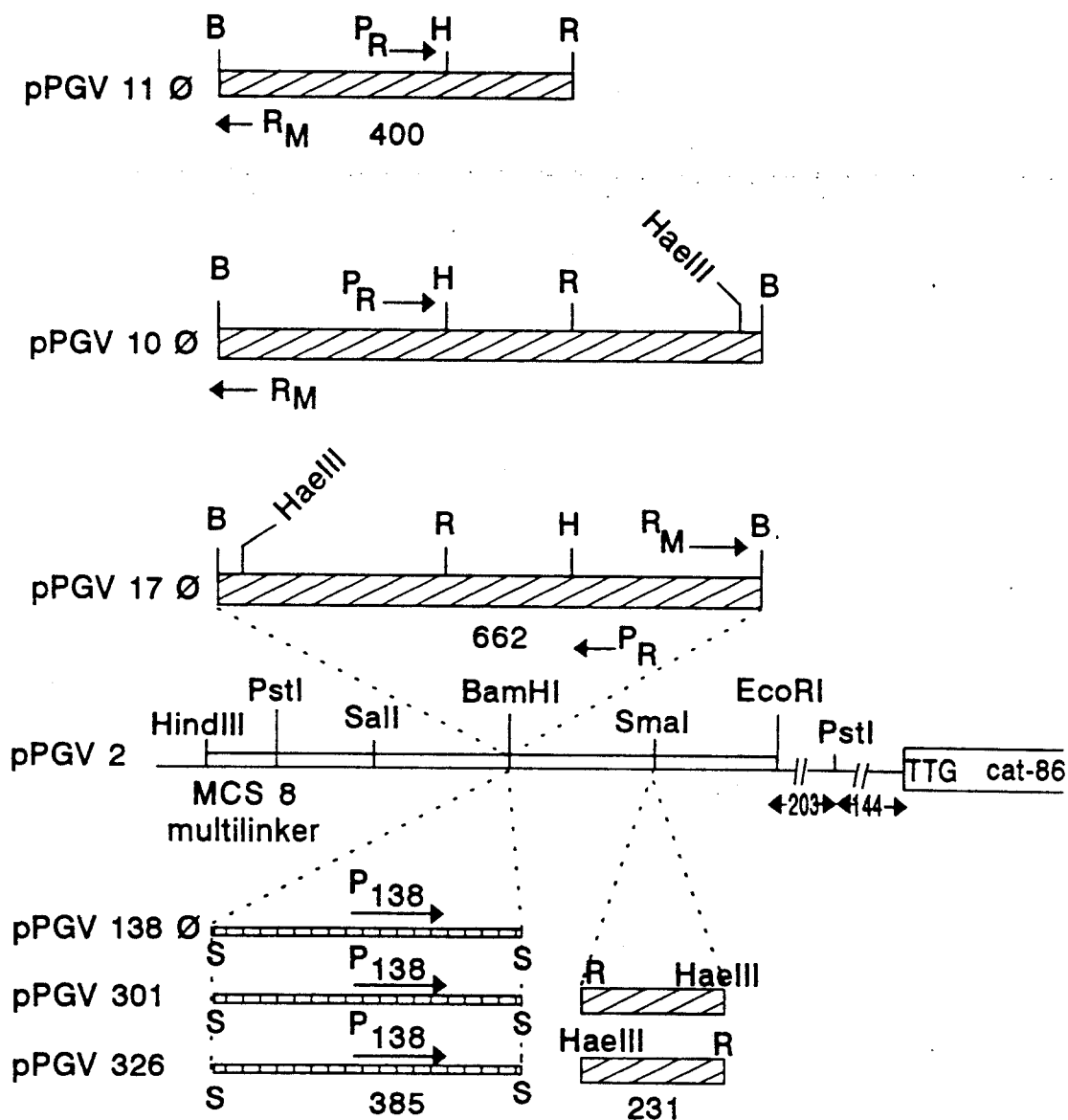
Figure 3:
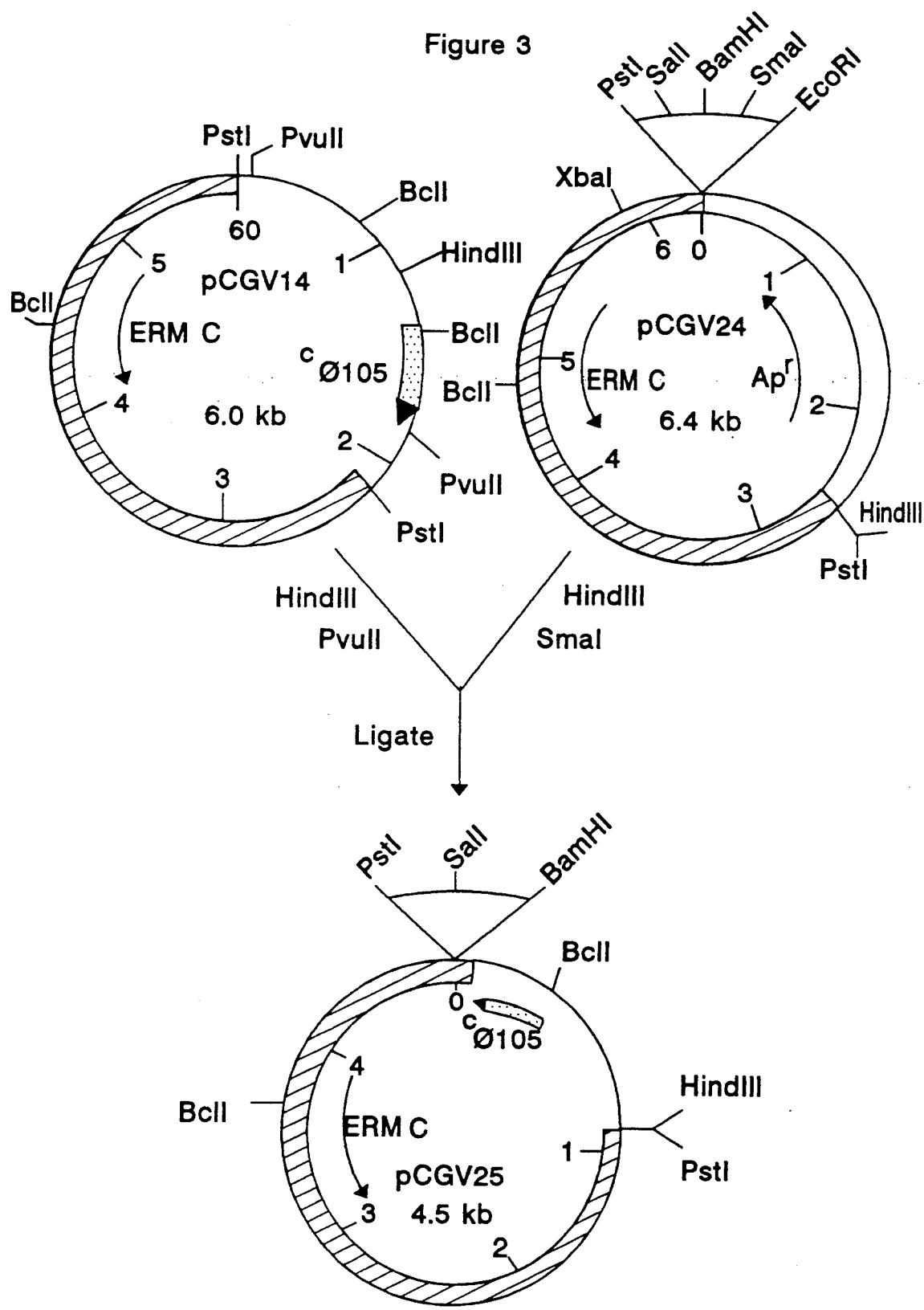

The invention is illustrated in and by the following experimental section and the accompanying drawings, in which FIG. 1a shows the EcoRI restriction map of $\phi 105$ DNA in the conventional orientation; the length of the fragments is indicated in kb (1000 basepairs); the 3.2 kb F fragment is shown as a black bar;

FIG. 1b shows a more detailed restriction map of the F fragment; the locations of the $\phi 105$ repressor gene ($c\phi 105$) and the ORF2 and ORF3 genes are shown, and so are the presumable extent of the immF region and the locations of the promoters $P_M$ and $P_R$; the 662 bp BclI fragment, analyzed in detail herein, is shown as a black bar; the scale is shown at the bottom;

FIG. 2 shows derivatives of the pPGV2 plasmid, which are provided with $\phi 105$ immF regulation sequences (black bars) upstream of the cat-86 gene (of which only the N-terminal part is shown); the BamHI and/or SmaI sites in the MCS8 element (shown enlarged) were used for making the insertions; the upper part shows the $P_R$-cat-86 fusions (pPGV11$\phi$ and pPGV10$\phi$) and a $P_M$-cat-86 fusion (pPGV17$\phi$), with the position and orientation of the promoters being indicated by small arrows; the pPGV11$\phi$ plasmid was constructed by replacing the BamHI-SmaI fragment of MCS8 by the 400bp BclI-RsaI fragment of $\phi 105$; the lower part shows the pPGV138$\phi$ plasmid (with the $P_{138}$ promoter) and derivatives thereof; the location and direction of the $P_{138}$ promoter are shown; the following restriction site abbreviations were used: B, BclI; H, HindIII; R, RsaI; S, Sau3A;

FIG. 3 schematically shows the construction of the repressor plasmid pCGV25; plasmid pCGV14, which contains the 2.3 kb PstI fragment I of $\phi 105$ (thin line) in the PstI site of pE194 cop-6 (thick line) is known from EP-A-0182562; plasmid pCGV24 is a bifunctional E. coli/B. subtilis plasmid which contains the origins of replication of pBR322 and pE194 cop-6; it was constructed by ligation of PstI treated pUC8 (double line) and pE194 cop-6 (thick line).

FIG. 4 shows the functional map and sequence of the regulation part of the $\phi 105$ immF region; part A schematically shows the transcription start sites (+1) and RNA polymerase recognition sites (−35, −10) of the $P_M$ and $P_R$ promoters. The black rectangles represent the 14 bp operator elements. The hatched regions represent coding regions. The map and sequence of the $\phi 105$ repressor gene have been reported before.

Part B shows the nucleotide sequence of the 662-bp BclI fragment (the same as indicated in part A). The upper strand is displayed only; the $P_M$ signals, the 5' end of the $P_M$ mRNA, and the first two codons of the repressor gene are shown in the antisense orientation. The nucleotides are numbered below the sequence. The $P_M$ and $P_R$ promotors are represented by their "−35" and "−10" regions (boxed) and their mRNA start positions (+1). The three 14-bp $O_R$ elements are also boxed, with a thicker line at the bottom. The $O_{R4}$ sequence (positions 82 to 95) is boxed by a broken line. Putative Shine-Dalgarno sequences are underlined. The amino acid numbers for the ORF3 polypeptide (taking leucine as +1) are shown to the right. The broken line under the amino acid residues 21–40 indicates the putative DNA-binding domain. The extent of the deletion (positions 445–477) in four operator-constitutive mutant isolates of pPGV301 is indicated by vertical broken-lined arrows.

Figure 5:
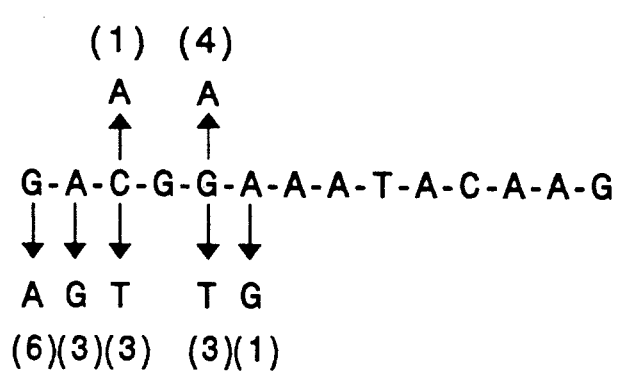

FIG. 5 shows the operator-constitutive ($O^c$) point mutations. Of the wild-type $O_R$ sequence, only one strand is shown with its 5'→3' orientation from left to right on the $\phi 105$ map, as displayed also in FIG. 4. In total, 25 mutants were characterized by sequence analysis. Of these, 21 exhibited point mutations. The identified base changes are indicated by vertical arrows. The number of independent $O^c$ colony isolates found to contain a particular mutation is indicated in brackets.

Figure 6:
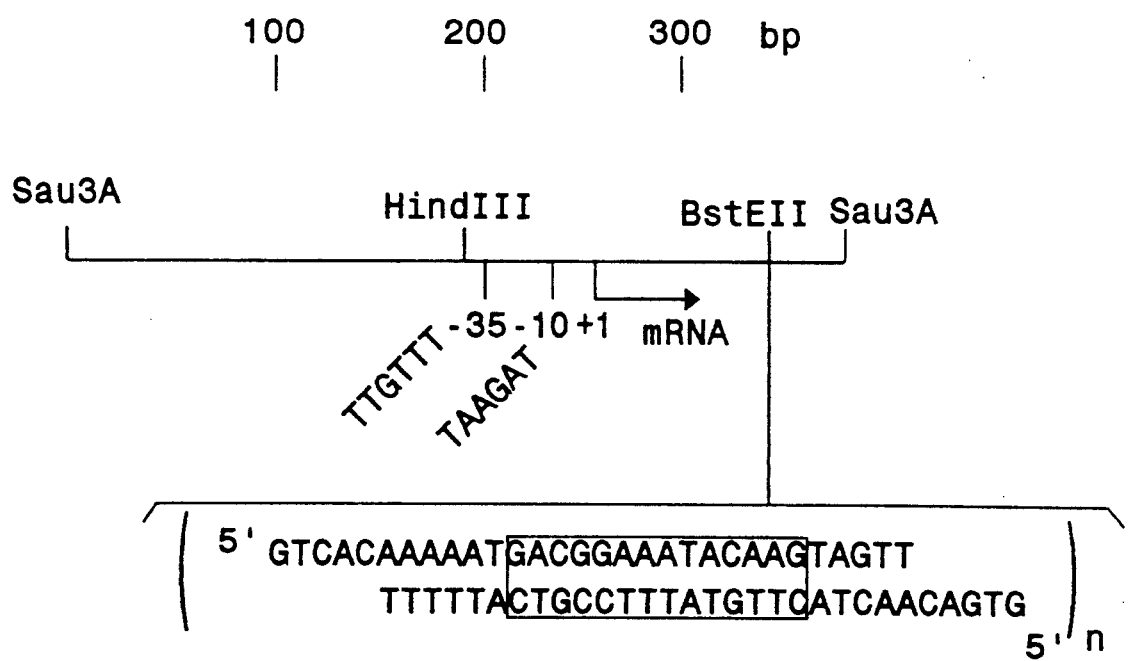

FIG. 6 shows the functional map of the $P_{138}$ fragment and the construction of $P_{138}$-(synthetic) $O_R$-cat-86 fusion derivatives of pPGV138 $\phi$; the 385-bp $P_{138}$ promoter fragment is shown in the same orientation as inserted in pPGV138$\phi$ (see FIG. 2). The $P_{138}$ promoter is represented by its RNA polymerase recognition sites (−35, −10) and the transcription start site (+1). The $P_{138}$-(synthetic) $O_R$-cat-86 fusion plasmids were derived from pPGV138; by inserting one or more copies (in direct repetition) of a 30-bp synthetic oligonucleotide in the unique BstEII site. The sequence of the synthetic $O_R$ fragment is shown in brackets. The actual 14-bp operator site is boxed. It is worth noting that the procruding 5'-ends of the oligonucleotide differ from each other in the third position.

FIG. 7 shows a comparison of the primary structure of the putative DNA-binding domains in the $\phi$105 repressor and the ORF3 polypeptide. The amino acids are shown by the well-known one-letter notation; the numbers indicate the positions of the amino acid residues in each sequence; identical amino acid residues are boxed, and conservative changes are indicated by a vertical line.

MATERIALS AND METHODS

(a) Bacterial Strains and Phages

*Bacillus subtilis* BR151 (trpC2,Lys3, metB10) was used as the host here. *B. subtilis* strain 168 (trpC2) and the corresponding wild-type $\phi$105 lysogen were obtained from the Bacillus Genetic Stock Centre (Ohio State University). *E. coli* strain MC1061, araB139, $\Delta$(ara, leu) 7697, $\Delta$lac$\chi$74, galU$^-$, galK$^-$, hsr$^-$, hsm$^+$, strA was used as the host for producing large quantities of plasmid DNA. All cultures were grown in Luria Broth (LB), supplemented with the appropriate antibiotics. Selective concentrations were: 200 /ug/ml ampicillin (Ap), 10 /ug/ml erythromycin (Em), 10 /ug/ml kanamycin (Km). Chloramphenicol (Cm) concentrations were variable and are indicated in the appropriate experiments.

(b) Construction of $\phi$105 Promoter and Repressor Plasmids

In the experiments, two compatible classes of recombinant plasmids were constructed and used. The pPGV series (promoter plasmids) essentially contain transcriptional fusions of $\phi$105 immF regulatory sequences to the coding region of the cat-86 (Cm$^R$) gene of *B. pumilus*. These plasmids (FIG. 2) are all derived from the bifunctional *E. coli/B. subtilis* promoter selection vector pPGV2. They carry the replication origins of pBR322 and pUB110 and, as selectable markers, contain Ap$^R$ (in *E. coli*) and Km$^R$ (in *E. coli* and *B. subtilis*).

The repressor plasmids (pCGV series) only replicate in *B. subtilis*. They were derived from the Em$^R$ multicopy vector pE194 cop-6 by the insertion of larger fragments from the $\phi$105 immF region. The pCGV14 plasmid is known from the earlier-cited European patent publication. The construction of pCGV25 is shown in FIG. 3. The plasmid contains the 740-bp HindIII-PvuII ImmF fragment (see FIG. 1) which essentially comprises the $\phi$105 repressor gene coding sequence plus 273 bp of the 5'-upstream region thereof.

(c) General recombinant DNA techniques

All procedures for plasmid DNA preparation, restriction, ligation, and transformation of competent *B. subtilis* or *E. coli* were as described in the cited European patent publication. The DNA sequences were determined using the Maxam & Gilbert method.

(d) Oligodeoxynucleotide Preparation

By means of an Applied Biosystems model 380A DNA synthesizer, the complementary single-strand oligodeoxynucleotides (30-mers) 5'-GTCACAAAAATGACGGAAATACAAG-TAGTT-3' and 5'-GTGACAACTACTTG-GTATTTCCGTCATTTTT-3' were chemically synthesized, using the phosphoramidite triester method of Beaucage & Caruthers. Purification was realized by Partisil 10-Sax anion exchange HPLC (High Performance Liquid Chromatography) and gel filtration through Sephadex G-100.

(e) Assays for Phage Infectivity

Phage infectivity tests were performed as described in the above-cited European patent publication, using wild-type $\phi$105 (109 pfu/ml).

(f) Mutagenesis with Nitrosoguanidine

For the mutagenesis, a modification of the Coulondre & Miller procedure was used. Exponentially growing cells of *B. subtilis* strain BR151, carrying the pPGV301 and pCGV25 plasmids, were spun down, washed with 0.1M sodium citrate buffer (pH 5.5) and resuspended in the original volume of citrate buffer. The cells were chilled on ice for 10 minutes and then placed in a water bath of 37° C. Nitrosoguanidine was added in a final concentration of 1 mg/ml. After appropriate periods, samples were taken, washed, and resuspended in the original volume of LB medium, which contained 10 /ug/ml Em and 5 /ug/ml Cm. The cells were incubated for 1 hour at 37° C. with aeration and plated on selective medium containing 10 /ug/ml Em and 50 /ug/ml Cm.

(g) RNA Isolation from *B. subtilis* and S1 Nuclease Mapping

Total RNA of *B. subtilis* cells, grown to midlog phase in LB medium, was purified by the hot-phenol extraction procedure of Aiba et al. DNA fragments to be used as probes were provided with a $^{32}$P label at the 5' end by means of T4 polynucleotide kinase and the strands were separated on 5% of 7.5% acrylamide gels (Maxam & Gilbert, 1980). Hybridization of RNA (10–20 /ug) to $^{32}$P-probe DNA (5–10 ng, 107 cpm//ug) and S1 nuclease digestion were accomplished as described by De Greve et al., 1982. Protected fragments were analyzed on 5% or 8% acrylamide-urea sequencing gels.

(h) Chloramphenicol Acetyl Transferase Activity Assays

*B. subtilis* cultures were grown to the late exponential phase and induced with 5 /ug/ml Cm for 30 minutes prior to harvesting. Extracts were prepared and analyzed for chloramphenicol acetyl transferase (CAT) activity as described in the above-cited European patent publication.

RESULTS

(a) S1 Nuclease Treatment for Mapping Two Divergent Promoters, $P_M$ and $P_R$ A 662-bp Bcl I (Sau3A) subfragment of EcoRI-F (FIG. 1) contains a repressible $\phi$105 promoter regulates transcription to the right on the conventional $\phi$105 map. The $\phi$105 immunity repressor gene (c$_{\phi 105}$) has been identified before, and its sequence is known. By deletion analysis of the 5'-upstream region of the repressor gene which is transcribed leftward, its promoter was found in the same BclI fragment. Accordingly, this fragment turns out to contain at least two promoters in opposite orientations. To confirm this and to precisely map the in vivo transcription start sites, total RNA was prepared from *B. subtilis* cells harbouring the $\phi$105 BclI fragment cloned in pPGV10$\phi$ (FIG. 2) and hybridized against each strand of the SalI-EcoRI plasmid fragment $^{32}$P-labelled at the 5'-end.

After S1 digestion, the protected fragments were separated on polyacrylamide gels. It was found that each strand of the probe protects an RNA fragment of a distinct size, which fragment is absent in control RNA prepared from *B. subtilis* cells containing the pPGV2 vector (results not shown). Transcription to the right, as represented by the band hybridizing to the lower 5'-$^{32}$P-EcoRI strand started some 420–440 bp from the right-hand end of the BclI fragment. The left-hand mRNA start site associated with the major band resulting from hybridization to the upper 5'-$^{32}$P-SalI strand mapped 55–60 bp from the left-hand end of the BclI fragment.

Both initiation sites were mapped at the nucleotide level, using each strand of a shorter probe, the SalI-EcoRI fragment of pPGV11φ and the Maxam-Gilbert sequencing products of the these strands as size markers. The base positions corresponding to the centre of each band of protected fragment were marked "+1" in the sequence of the BclI fragment (see FIG. 4, part B). The position of the left-hand start site (nucleotide 59) defines the promoter for the $c_{\phi 105}$-ORF2 transcription unit and agrees perfectly with previous results from a Ba131 deletion analysis in this region. This promoter is here designated $P_M$. The "−35" and "−10" recognition sites are shown in FIG. 4, part B. As only the upper strand of the BclI fragment is shown, the $P_M$ signals are represented by the antisense strand.

The right-hand transcription start site (nucleotide 235) enables the identification of the promoter under negative control of the φ105 repressor. The corresponding RNA polymerase recognition sites are also shown in FIG. 4, part B. This promoter is termed herein $P_R$. The proximal gene transcribed from $P_R$ specifies a 89 amino acid polypeptide (ORF3), which is the topological equivalent of λcro. The sequence of its translation product is also shown in FIG. 4, part B. The results of the S1 study further showed that the $P_R$ transcript extends beyond the right-hand end of the BclI fragment and that there is no other transcription initiation site between the ORF3 stop codon and the BclI site. Mainly by analogy with phage λ, it would appear that $P_R$ may be assumed to regulate the initiation of a polycistronic mRNA involved in the onset of the lytic route. Both $P_M$ and $P_R$ have "−35" and "−10" sites conforming to the consensus sequence for a promoter recognized by the major vegetative form (Eo$^{43}$) of *B. subtilis* polymerase. In both cases the hexanucleotides are separated by 17 bp.

(b) The Product of $c_{\phi 105}$ Suppresses $P_R$, but Stimulates $P_M$

To assess the effect of φ105 repressor in trans on the activity of $P_M$ and $P_R$, transcriptional fusions were constructed between each of these promoters and the cat-86 gene. The constructs, all derived from pPGV2, are shown in FIG. 2. The $P_R$-cat-86 fusion plasmid pPGV10φ has been described before. In another $P_R$-cat-86 fusion (pPGV11φ) the 400-bp BclI-RsaI fragment was used, eliminating the C-terminal part of ORF3 and the 3'-untranslated sequence thereof.

The plasmid pPGV17φ carries a $P_M$-cat-86 fusion and was obtained simply by recloning the entire BclI fragment in reverse orientation.

Subsequently, the cat-86 expression of each of these plasmids in *B. subtilis* cells was examined, both in the absence and in the presence of φ105 repressor. To provide functional repressor in trans, a 740-bp φ105 fragment, extending from the HindIII site (position 273 in FIG. 4, part B) leftwards to a PvuII site immediately downstream of the stop codon of the repressor gene (FIG. 1) was cloned in the compatible, Em$^R$ plasmid pE194 cop-6, yielding pCGV25. It has been shown before that this fragment is sufficient to produce a functional $c_{\phi 105}$ product. Accordingly, *B. subtilis* (pCGV25) transformants were immune against φ105 infection. A rough indication of the effect of $c_{\phi 105}$ expression on transcription in both types of fusions was obtained by growth tests on plates containing antibiotic. Whereas strains containing pPGV10φ or pPGV11φ ($P_R$ fusions) were found to be resistant to chloramphenicol (15 /ug/ml), the introduction of pCGV25 in these strains resulted in double transformants with an Em$^R$Cm$^S$ phenotype. The opposite was observed for pPGV17φ ($P_M$ fusion): cells containing this plasmid only were Cm$^S$, and the introduction of pCGV25 resulted in double transformants with an Em$^R$Cm$^R$ phenotype (see Table A).

TABLE A

Chloramphenicol resistance (15 ug/ml) and cat-86 activity (umol/hr. mg protein) of *B. subtilis* BR151 harbouring the indicated plasmids

| Repressor plasmid | Promoter plasmid | | | | | |
|---|---|---|---|---|---|---|
| | pPGV10φ | | pPGV11φ | | pPGV17φ | |
| | Cm$^R$ | cat-86 activity | Cm$^R$ | cat-86 activity | Cm$^R$ | cat-86 activity |
| None | + | 13.6 | + | 56.5 | − | 1.0 |
| pE194 cop-6 | + | N.D. | + | 52.7 | − | 1.0 |
| pCGV25 | − | 2.3 | − | 7.7 | + | 30.6 |

Cm$^R$, chloramphenicol resistance; N.D., not determined.

in regulation takes place at the level of transcription, the earlier-described S1 nuclease experiment was repeated, this time using RNA prepared from cells which in addition to pPGV11φ either did or did not contain pCGV25. It was found that the amount of mRNA transcribed from $P_R$ was reduced to a virtually undectable level in the presence of φ105 repressor. The $P_M$ transcript, on the contrary, was considerably more abundant in the double transformant. (Results not shown herein.) For both promoters, the position of the mRNA start site is unaltered, the $c_{\phi 105}$ product does not appear to induce changes in the specificity with which the *B. subtilis* host RNA polymerase recognizes the promoter.

(c) Presence of Three Identical 14-bp Sequences in Direct Repetition

In order to find the molecular basis for the observed effects of φ105 repressor on transcription from $P_M$ and $P_R$, the sequence of the 662-bp BclI fragment (see FIG. 4, part B) was carefully inspected. A striking observation was made, namely, that a 14-bp sequence, 5'-GACGGAAATACAAG-3' occurs thrice in this fragment in direct repetition. Two copies are located close together in the non-transcribed region between $P_M$ and $P_R$ (nucleotide position 105-118 and 135-148, respectively). The third element is found at a considerable distance to the right, within the coding sequence of ORF3 (nucleotides 459–472). Because it is very unlikely that such an arrangement occurs by chance, it was considered worthwhile to examine whether these 14-bp sequences are involved in the transcriptional control exerted by the φ105 repressor.

The following experiments provide evidence for the correctness of this suppossision. As the three sequences are identical, it was examined whether the φ105 repressor is capable of interacting with one of these elements.

For this purpose, $O_{R3}$ was selected, as this copy is contained within a 231-bp RsaI-HaeIII fragment (see FIG. 4), by virtue of which $O_{R3}$ can easily be isolated from the other two 14-bp elements.

(d) Construction and Properties of a Hybrid Promoter-$O_{R3}$ Control Element To examine the functional role of $O_{R3}$, the 231-bp RsaI-HaeIII fragment was inserted between a constitutive promoter and the cat-86 gene, whereafter the cat-86 expression from such a hybrid construct in *B. subtilis* cells which did or did not contain $\phi 105$ repressor was assayed. In designing this construct, care was taken that the distance between the constitutive promoter and the RsaI-HaeIII fragment was comparable to the natural distance from $P_R$ in the $\phi 105$ genome.

To this end, plasmid pPGV183$\phi$ was used, which was derived from pPGV2 by insertion, in the BamHI site of a 385-bp Sau3A fragment containing a strong *B. subtilis* promoter (see FIGS. 2 and 6). The plasmid pPGV138$\phi$ gives a high Cm resistance (>50 /ug/ml) in *B. subtilis*. The precise origin of the promoter (from a phage or from the chromosome) is unknown. It is clear, however, that the promoter is not derived from the $\phi 105$ immunity region and its activity remains unaltered in the presence of $\phi 105$ repressor. Consequently, within the range of the studies conducted, the promoter could be regarded as constitutive, and will be designated herein as $P_{138}$. The transcriptional start site within the 385-bp fragment was mapped by S1 nuclease analysis (data not shown), permitting full characterization of $P_{138}$ by its "−35" and "−10" hexanucleotides (see FIG. 6). The structure of these signals (TTGTTT and TAAGAT, respectively, separated by 17-bp) suggests that $P_{138}$, like $P_M$ and $P_R$, is recognized by a $E\sigma^{43}$ polymerase.

Two plasmids derived from pPGV138$\phi$ were obtained for insertion of the $O_{R3}$ containing RsaI-HaeIII fragment in both orientations in the unique SmaI site located 157-bp downstream of the $P_{138}$ mRNA start position. It is worth noting that the natural distance between the $P_R$ start site and the RsaI cleavage site in the $\phi 105$ immF region (see FIG. 4, part B) is only a little larger (165 bp). The plasmid pPGV301 contains the fragment in its original orientation, whereas pPGV326 contains the inverted (HaeIII-RsaI) sequence (see FIG. 2). Each of these plasmids were introduced into two *B. subtilis* acceptors, which were isogenic except as regards the presence or absence of pCGV25. The results of CAT activity determinations on the single and double transformants (Table B) show that expression of the cat-86 in pPGV301 is reduced at least 15-fold in the presence of, but not in the absence of pCGV25. The CAT activity of the control plasmid pPGV138$\phi$ was found not to be significantly altered after introduction of the repressor plasmid. Whereas, accordingly, the insertion of the RsaI-HaeIII fragment per se did not affect cat-86 expression, a significant reduction is observed when $\phi 105$ repressor is provided in trans. A slightly different effect was observed with pPGV326. In this case, a 2- to 3-fold reduction of CAT activity is observed even in the absence of repressor (cf pPGV326 with pPGV138$\phi$ and pPGV301). In the double transformant with pCGV25, only a 4-fold extra repression was measured, as compared to cells containing pPGV326 alone.

The quantitative data are further expressed in the phenotypes of the above-mentioned strains on antibiotic plates: *B. subtilis* cells just containing pPGV138$\phi$ or pPGV301 are resistant to 50 /ug/ml Cm, whereas pPGV326 imparts resistance against only 25 /ug/ml. Furthermore, a double transformant containing both pCGV25 and pPGV138$\phi$ exhibits an $Em^R Cm^R$ (50 /ug/ml) phenotype, whereas a strain containing pCGV25 and pPGV301 is $Em^R Cm^S$ (50 /ug/ml), with the Cm resistance is reduced to 15 /ug/ml.

These data suggest that the $\phi 105$ repressor does indeed exhibit interaction with the 231-bp $O_{R3}$ containing immF fragment, with transcription from an upstream promoter being reduced. This effect appears to be most outspoken when the $O_{R3}$ fragment maintains its original orientation relative to the transcriptional direction.

One complication inherent in the use of cat-86 as an indicator gene is the Cm inducibility of its expression at post-transcription level. Accordingly, measurements of the CAT activity are probably not an accurate reflection of the transcriptional effectivity of strong promoters such as $P_{138}$, because the inducing Cm concentration used in the assay (5 /ug/ml) is perhaps not sufficient for a complete induction of the available cat-86 mRNA. The values obtained in the absence of pCGV25 (Tables A and B) are therefore probably too low. This supposition was corroborated by replacing the cat-86 gene by xylE of *Pseudomonas putida*. In this case xylE expression of an identical $p_{138}$-$O_R$ hybrid control element, as in pPGV301, was reduced more than 100-fold (compared to 23-fold for cat-86; see Table B) in the presence of $\phi 105$ repressor (results not shown).

(e) Isolation and Mapping of Operator-Constitutive Mutations

Operator sequences can be genetically characterized by cis-dominant mutations that destroy their repressor binding ability. Such mutants are termed operator-constitutive ($O^c$). A number of such mutants have now been generated and isolated using the *B. subtilis* strain containing both pCGV25 and pPGV301. The combination of these two plasmids in the same cell results in an $Em^R Cm^S$ (50 ug/ml) $\phi 105^{imm}$ phenotype, because the $\phi 105$ repressor produced by the $Em^R$ plasmid exhibits interaction with the 231-bp immF RsaI-HaeIII fragment to decrease cat-86 expression as shown above. Any mutation eliminating this interaction would therefore yield a selectable, high-level $Cm^R$ phenotype. After nitrosoguanidine mutagenesis and subsequent selection for $Em^R$ and $Cm^R$ (50 /ug/ml) cells, two types of plasmid linked mutations were expected; (i) pCGV25 repressor mutations and (ii) operator mutants of pPGV301. These types can be easily distinguished, since the first type of mutations should exhibit loss of immunity against $\phi 105$ infection, whereas in the second type of mutations this phenotype should remain unaltered.

Of a total of 437 originally obtained $Em^R Cm^R$ colonies, 246 had retained immunity against $\phi 105$ infection. Plasmid DNA prepared from each of these $Em^R Cm^R$ $\phi 105^{imm}$ mutants was examined for its ability to transform a *B. subtilis* [pCGV25] acceptor to high-level $Cm^R$ with a high frequency. Mutants in which the $Cm^R$ phenotype was found to be plasmid-linked were retained for further examination. The mutations in each pPGV301 derivative were mapped by sequence analysis across the 231-bp $\phi 105$ immF fragment containing $O_{R3}$.

As a result, 21 of the 25 independent mutants that were examined showed single-base alterations within the 14-bp sequence (see FIG. 5). The remaining 4 mutants had suffered the same deletion, a loss of 33 bp, as a result of which the entire 14-bp element was removed (see FIG. 4, part B). It is striking that all point mutations, both transitions and transversions, involve the 5'-proximal part of the 14-bp sequence (positions 1, 2, 3, 5 and 6).

(f) A Chemically Synthesized $O_R$ Sequence is Functional as an Operator

As a definite proof for the supposed operator function of the 14-bp repeat, a double-stranded oligodeoxynucleotide containing the 14-bp sequence was prepared by chemical synthesis, and this DNA was subsequently inserted between the constitutive promoter ($P_{138}$) and the cat-86 gene. In the 30-bp synthetic DNA fragment (FIG. 6), the $O_R$ sequence is flanked at both sides by a few spacer nucleotides, corresponding to those naturally surrounding the $O_{R3}$ copy, and by protruding 5'-ends forming a BstEII cleavage site. The synthetic, 5'-phosphorylated double-stranded piece of operator DNA was ligated to pPGV138φ, cleaved at its unique BstEII site. This site is located within the 385-bp Sau3A promoter fragment, 139 nucleotides downstream of the in vivo $P_{138}$ transcription start site (see FIG. 6).

A series of recombinant plasmids was isolated, containing one to several copies of the 30-bp fragment cloned in direct repetition, as verified by DNA sequence analysis across the insert (due to the 1-bp difference between the individual BstEII ends, the formation of inverted repeat structures is probably unfavourable). The individual 14-bp elements in the multiple $O_R$ constructs are separated by 16-bp, which is exactly the natural distance between the $O_{R1}$ and $O_{R2}$ sites in the φ105 genome.

The hybrid $P_{138}$-$(O_R)_n$-cat-86 plasmids with n=1, n=2, n=3, and n=5 (Table B) were subsequently transferred to B. subtilis BR151 containing pCGV25, and to isogenic cells without repressor plasmid. To determine whether the insertion of a single or multiple copies of the $O_R$ is (are) sufficient for cat-86 expression to be under negative control by the $c_{φ105}$ product, the CAT activities were determined for these strains.

Before interpreting the results shown in Table B, it should be noted that only a fraction of the repressor synthesized in the double transformants can be expected to be available for interaction in trans with the synthetic operator site or sites. The reason is that pCGV25 itself contains both $O_{R1}$ and $O_{R2}$, which are located within the φ105 HindIII-PvuII fragment. The copy number of pCGV25 (a derivative of pE194 cop-6) is at least comparable to, and possibly larger than, that of the pPGV138φ::$(O_R)_n$ plasmids. It may accordingly be supposed that a considerable amount of repressor will bind in cis upstream of its own gene.

Nevertheless, Table B shows that a single copy of the synthetic operator is sufficient to reduce the cat-86 expression more than 3-fold in the presence of, but not in the absence of, pCGV25. It is also clear that the observed repression increases with the number of cloned $O_R$ elements, reaching a 23-fold reduction of CAT activity for the $P_{138}(O_R)_5$ construct. Although these results demonstrate the functionality of the 30-bp oligonucleotide as an operator, it cannot as yet be assessed at this stage whether there is any cooperative repressor binding in the case of such tandemly arranged $O_R$ elements.

(g) Isolation and Characterization of a Temperature-Sensitive Repressor Mutant One of the most suitable methods of controlling the expression of cloned genes in an efficient manner is the use of temperature-sensitive repressor variants. Such repressors are capable of binding to the operator at low temperature (28° C.), but at higher temperature (42° C.) the operator/repressor interaction is broken. Genes cloned at the low temperature can then be expressed after an increase in temperature.

TABLE B

| | Cat-86-specific activities (umol/hr · mg protein) of B. subtilis BR151 harbouring the indicated plasmids [a] | | |
|---|---|---|---|
| | cat-86 activity | | x-fold |
| Promoter plasmid | −pCGV25 | +pCGV25 | repression |
| pPGV138φ | 487 | 474 | 1.0 |
| pPGV301 | 493 | 29 | 16.6 |
| pPGV326 | 195 | 46 | 4.3 |
| pPGV138φ::$(O_R)_1$ | 317 | 105 | 3.1 |
| pPGV138φ::$(O_R)_2$ | 386 | 47 | 8.2 |
| pPGV138φ::$(O_R)_3$ | 308 | 26 | 11.9 |
| pPGV138φ::$(O_R)_5$ | 342 | 13 | 23.3 |

[a] Each value presented is the average of at least two independent assays.

In order to isolate temperature-sensitive repressor mutants by selection, a method was used which is very similar to that used in the isolation of operator-constitutive mutants. Now, however, a new repressor plasmid construct was made, namely, pCGV38. pCGV38 was derived from pCGV25 by replacing the $P_M$ promotor by $P_{138}$, so that transcription of the repressor gene becomes constitutive. After nitrosoguanidine mutagenesis of a B. subtilis strain containing both pCGV38 and pPGV301, selection tests were made for simultaneous $Em^R$ and $Cm^R$ (50 /ug/ml). Temperature-sensitive mutants were then identified by φ105 infectivity tests at low (28° C.) and high (42° C.) temperature. Mutants with such a phenotype are phage-resistant at 28° C. and phage-sensitive at 42° C.

5 of the 2000 mutants examined were found to have the desired properties. These temperature-sensitive mutants were characterized further by DNA sequence analysis. In each case the same point mutation had occurred, a G-to-A change in codon 4 of the repressor gene. This changes the fourth amino acid in the polypeptide from glycine (G) to glutamic acid (E). The new plasmid coding for this temperature-sensitive repressor was called pCGV38GE4.

Subsequently, the suitability of pCGV38GE4 for use in regulated gene expression was studied. pCGV38GE4 was combined in the same cell with different promoter-operator plasmids (pPGV11φ, pPGV301 and pPGV138φ::$(O_R)_5$). The chloramphenicol resistance of these strains was investigated at 28° C. and 42° C. A B. subtilis strain containing both pCGV38GE4 and pPGV11φ is $Cm^S$ at 28° C. and $Cm^R$ (15 /ug/ml) at 42° C. Strains containing, on the one hand, pCGV38GE4 and, on the other hand, pPGV301 or pPGV138φ::$(O_R)_5$ are $Cm^R$ at the two temperatures. These results show that the repression exerted by the temperature-sensitive pCGV38GE4 repressor mutant at 28° C. is only sufficient to accomplish a temperature-inducible synthesis of the cat-86 gene product in combination with pPGV11φ.

A possible explanation for these results can be found in the fact that in pPGV11φ, pPGV301 and pPGV138φ::$(O_R)_5$ the number of operator(s) and their relational position relative to the promoter are different. pPGV11φ contains 2 operators ($O_{R1}$ and $O_{R2}$) upstream of $P_R$. pPGV301 and pPGV138φ::($O_R$)5 respectively contain 1 and 5 operators ($O_{R3}$) upstream of $P_{138}$. Probably, the precise configuration of the promoter-operator construct is very important to provide sufficient repression at low temperature and, hence, temperature induction.

Finally these results were extended by assays of the CAT enzymatic activity at different temperatures (28° C., 33° C., 37° C. and 42° C.). The results are summarized in Table C. The CAT activity of cells containing both pPGV11φ and pCGV38GE4 increases with increasing temperature. The CAT activity of this strain at 42° C. is at least 3 times higher than at 28° C. As a control, the same assays were conducted for a strain containing pPGV11φ and pCGV38. In this case the CAT activity was substantially the same at all tempatures.

TABLE C

CAT-specific activity (μmole/hour × mg protein) of B. subtilis BR151 strains containing the plasmids designated.

|  | 28° C. | 33° C. | 37° C. | 42° C. |
|---|---|---|---|---|
| pPGV11φ + pCGV38 | 12.8 | 14.4 | 9.63 | 10.7 |
| pPGV11φ + pCGV38GE4 | 18.4 | 24.7 | 38.8 | 61.4 |

I claim:

1. A method of regulating the expression of a structural gene in a *Bacillus subtilis* which comprises:
   (a) transforming the *Bacillus subtilis* with one or more recombinant plasmids including a plasmid comprising a gene encoding a temperature-sensitive phi 105 repressor and the same plasmid or a second plasmid comprising the structural gene whose expression is to be regulated operably linked to a promoter and phi 105 operator DNA sequence, wherein the phi 105 operator DNA sequence is positioned about 220 bp downstream of the promoter, has no two-fold rotational symmetry, is made at least in part by chemical synthesis and is selected from the group consisting of the 14-bp sequence 5'-GACGGAAATACAAG-3', the 14-bp sequence 5'-GTCGGAAATACAAT-3', the 13-bp sequence 5'-GACGAAATTCAAG-3' or the 14-bp sequence 5'-GTCGTGAATACCAT-3'; and p1 (b) growing the transformed *Bacillus subtilis* under low temperature conditions to inhibit expression of the structural gene or under high temperature conditions to allow expression of the structural gene.

2. The method of claim 1, wherein the second plasmid comprises a plurality of copies on tandem of the operator DNA sequence.

3. The method of claim 1, wherein the second plasmid comprises two or more copies of the operator DNA sequence, one of which is positioned upstream of the promoter.

* * * * *